United States Patent
Mooshofer

(10) Patent No.: US 7,661,314 B2
(45) Date of Patent: Feb. 16, 2010

(54) METHOD AND SYSTEM FOR DEFECT INVESTIGATION OF COMPONENT

(75) Inventor: Hubert Mooshofer, Nürnberg (DE)

(73) Assignee: Siemens Aktiengesellschaft, Munich (DE)

(*) Notice: Subject to any disclaimer, the term of this patent is extended or adjusted under 35 U.S.C. 154(b) by 198 days.

(21) Appl. No.: 11/540,649

(22) Filed: Oct. 2, 2006

(65) Prior Publication Data

US 2007/0079645 A1 Apr. 12, 2007

(30) Foreign Application Priority Data

Sep. 30, 2005 (DE) ............... 10 2005 047 536

(51) Int. Cl.
*G01N 29/04* (2006.01)
(52) U.S. Cl. ..................... 73/611; 73/629
(58) Field of Classification Search ............. 73/611, 73/614, 629, 631
See application file for complete search history.

(56) References Cited

U.S. PATENT DOCUMENTS

| 4,510,811 A | * | 4/1985 | Sternberg et al. ............ 73/611 |
| 5,507,184 A | | 4/1996 | Freund et al. |
| 5,623,100 A | * | 4/1997 | Arima et al. ................. 73/611 |

FOREIGN PATENT DOCUMENTS

DE 42 23 502 A1 1/1994

* cited by examiner

*Primary Examiner*—John E Chapman
(74) *Attorney, Agent, or Firm*—Staas & Halsey LLP

(57) ABSTRACT

One surface of a component is obliquely ensonified through a liquid or gaseous first medium with a checking sound beam produced by a transmission/reception transducer for defect investigation of the component. A response sound beam, which is reflected back from the surface to the transmission/reception transducer, is received and its delay time in the medium between the transmission/reception transducer and the surface is evaluated. The delay time in the medium determined in this way is taken into account for localization of a defect within the component.

5 Claims, 3 Drawing Sheets

METHOD AND SYSTEM FOR DEFECT INVESTIGATION OF COMPONENT

CROSS REFERENCE TO RELATED APPLICATIONS

This application is based on and hereby claims priority to German Application No. 10 2005 047 536.1 filed on Sep. 30, 2005, the contents of which are hereby incorporated by reference.

BACKGROUND

A method for defect investigation of a component is described in which one surface of the component is obliquely ensonified through a liquid or gaseous first medium with a checking sound beam produced by a transmission/reception transducer. The method is performed by a system for defect investigation of a component that includes a transmission/reception transducer which produces a checking sound beam and is designed to obliquely ensonify one surface of the component through a liquid or gaseous first medium with the checking sound beam, and to receive a response sound beam which is reflected back from the surface to the transmission/reception transducer.

Methods and systems such as these for defect investigation of a component, in particular for ultrasound testing, are known in a wide range of embodiments. In order to allow defects close to a surface to be identified, the sound is injected obliquely, so that the injection direction differs from the normal to the surface of the component to be investigated. Water is normally, but not exclusively, used as the first medium. This immersion technique results in very good coupling between the checking sound beam and the component to be investigated. Furthermore, there is no direct contact between the component and the transmission/reception transducer, so that the surface of the component is not mechanically loaded.

However, it is initially not known when the checking sound beam will strike the surface and the actual recording of the component will thus start. The transmission/reception transducer is therefore placed—provided that the surface contour allows this—at an exactly adjusted distance from the component, or is readjusted during operation corresponding to the surface contour as determined in advance, in order to keep the distance from the component approximately constant. Furthermore, it is possible to determine the distance to the component using a separate measurement device element. This last variant is described, for example, in DE 42 23 502 A1. In addition to the obliquely injecting transmission/reception transducer, an additional, vertically injecting, transmission/reception transducer is provided. All three variants are, however, associated with considerable implementation complexity.

SUMMARY

One aspect is to specify a method of the type described initially which can implemented with little complexity.

According to the method described in more detail below, a response sound beam, which is reflected back from the surface to the transmission/reception transducer, is received and its delay time in the medium between the transmission/reception transducer and the surface is evaluated, the delay time in the medium determined in this way is taken into account for localization of a defect within the component, and a different transmission condition or a different reception condition is in each case used for determination of the delay time in the medium and for defect localization.

In the method described in more detail below, the delay time in the medium which is required for passage twice through the first medium is determined using a response sound beam, which is reflected back in particular as a result of the surface roughness in the direction of the transmission/reception transducer. In particular, this is a scattered component, whose intensity is considerably less than that of the main surface reflection, or else that of a defect reflection. Nevertheless, this weak scatter component is virtually always present. This is advantageously used in the method described in more detail below to determine the delay time between the transmission/reception transducer and the surface. The delay time in the medium which is required for further evaluation, in particular for defect localization, is thus determined with comparatively little implementation complexity. In particular, no complex adjustment or readjustment of the transmission/reception transducer or a separate measurement device element is required, as in the case of the known methods.

A different transmission condition or a different reception condition are in each case used to determine the delay time in the medium and for defect localization. Furthermore, a combination of both measures is also possible. In this way, the transmission mode and/or reception mode are/is matched to the response sound beam, whose intensity is normally only very weak and which is reflected back from the surface, having been produced in particular by scattering mechanisms on surface roughness features. This allows the delay time in the medium that is sought to be determined better.

In one advantageous variant, a result of the evaluation is used for adaptation of a transmission condition or of a reception condition. This is done in particular automatically, that is to say adaptively. Adaptation is then carried out only on a requirement-controlled basis, and also only until the delay time in the medium has been determined with adequate confidence.

According to another preferred variant, the determination of the delay time in the medium and the defect localization are carried out alternately. Both investigations can then be carried out with respectively matched transmission and/or reception conditions, thus producing more accurate results. In addition, alternate delay-time determination and defect localization are particularly advantageous when the transmission/reception transducer and the component to be investigated are being moved relative to one another, as is normally the case during an investigation of the entire component. The respectively specific delay time in the medium is then determined for each local measurement point. Delay-time differences which are caused by the surface contour of the component are taken into account in this way.

The transmission condition is furthermore preferably adapted by influencing the checking sound beam. A plurality of preferred variants are possible for this purpose. In the case of the first, a beam diameter of the checking sound beam is varied and, in particular, is reduced in order to determine the delay time in the medium. This makes it possible to achieve at least partial focusing on the surface, thus making it possible to achieve a greater intensity in the response sound beam. In particular, the beam diameter and thus the focusing can be varied by using a transmission/reception transducer in the form of an array test head.

In the second preferred variant, the transmission amplitude of the checking sound beam is varied, and in particular is increased in order to determine the delay time in the medium. This measure leads directly to an increase in the intensity and the resultant response sound beam, as well.

In the third preferred variant, the signal form of the checking sound beam is varied. In this case, a burst signal form is set, in particular, in order to determine the delay time in the medium, instead of the otherwise normal short transmission pulse form. The energy content of the checking sound beam can be varied as a function of the time duration of the burst signal, thus once again resulting in the response sound beam being of adequate intensity.

The three preferred variants mentioned above for influencing the checking sound beam may be used individually or else in combination with one another.

In an expedient further refinement, the gain factor is varied at the reception end and, in particular, is increased in order to determine the delay time in the medium. This therefore relates to an adaptation of the reception condition, so that it is also possible to identify a relatively low intensity response sound beam, which results from scattering on surface roughness features.

A further aspect is to implement the method using a system with little complexity. The system described in more detail below includes a control and evaluation unit which is connected to the transmission/reception transducer and is designed to evaluate the delay time of the response sound beam in the medium between the transmission/reception transducer and the surface, to take account of the delay time in the medium determined in this way for localization of a defect within the component, and to respectively use a different transmission condition or a different reception condition for the determination of the delay time in the medium and for defect localization.

BRIEF DESCRIPTION OF THE DRAWINGS

These and other aspects and advantages will become more apparent and more readily appreciated from the following description of exemplary embodiments, taken in conjunction with the accompanying drawings of which.

DETAILED DESCRIPTION OF THE PREFERRED EMBODIMENT

Figure 1:
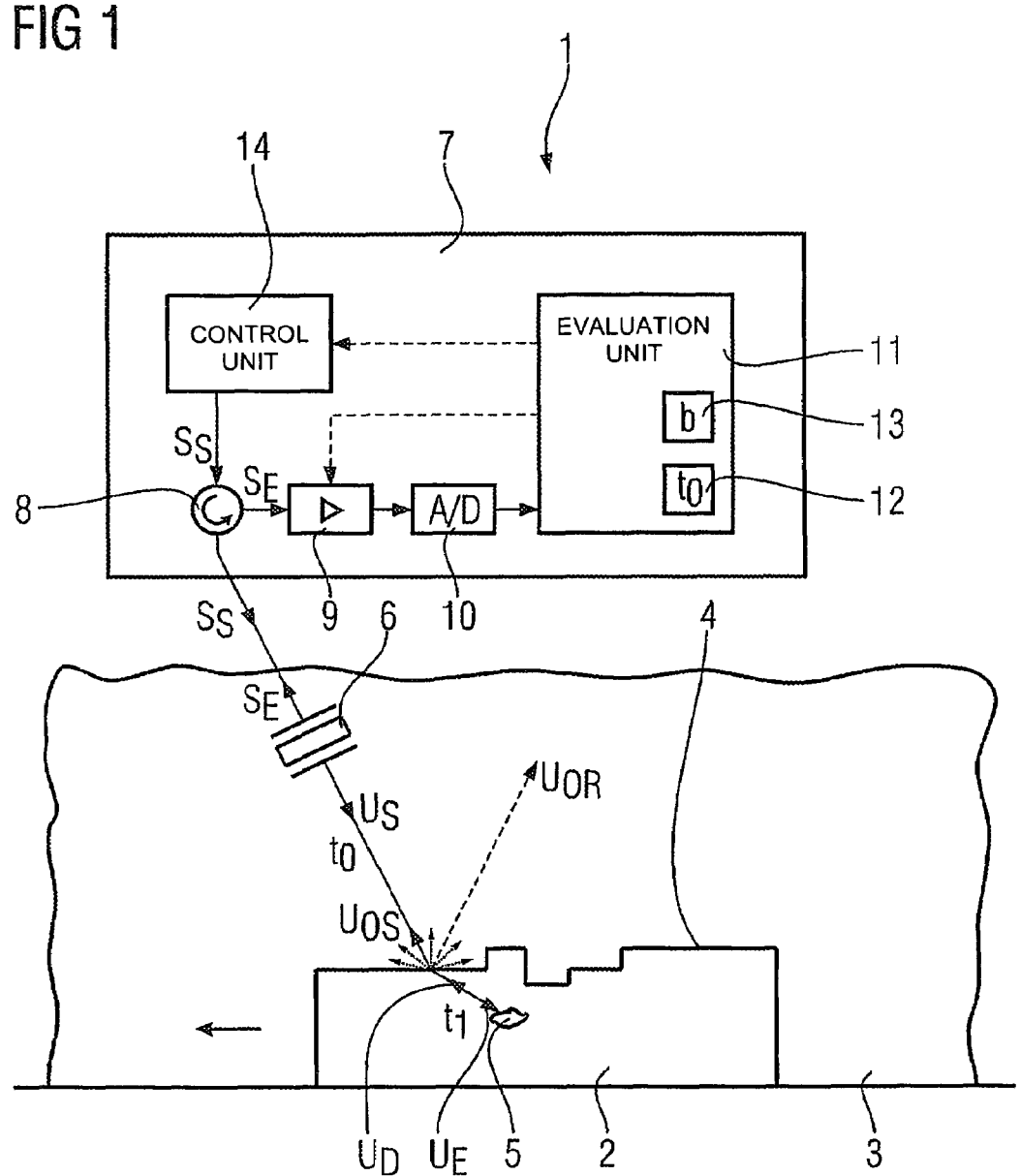
FIG. 1 is a block diagram of an exemplary embodiment of a system for defect investigation of a component using ultrasound, and having a sub unit for determination of the delay time in a medium.

Reference will now be made in detail to the preferred embodiments, examples of which are illustrated in the accompanying drawings, wherein like reference numerals refer to like elements throughout.

FIG. 1 shows one exemplary embodiment of an arrangement 1 for defect investigation of a component 2 using ultrasound. The component 2 is immersed in a first medium 3 which, in the exemplary embodiment, is water. However, in principle, it is also possible to use a different liquid, such as oil, or else a gas. The component 2 to be investigated is essentially not subject to any restrictions. It may have a smooth or, as indicated in the exemplary embodiment, a contoured surface 4. A defect 5 which is intended to be localized by the arrangement 1 is located at an initially unknown point within the component 2.

The arrangement 1 also has a transmission/reception transducer 6, which is electrically connected to a control and evaluation unit 7. The transmission/reception transducer 6 is also located within the first medium 3, or is at least directly coupled to it. This is in the form of an ultrasound transducer.

The control and evaluation unit 7 has a transmission/reception duplexer 8 for separation of the transmission side and reception side. An amplifier 9, an analog/digital converter 10 and an evaluation unit 11 are provided on the reception side, are connected in series in this sequence, and are connected to the transmission/reception duplexer 8. The evaluation unit 11 contains a delay-time sub unit 12 and a defect sub unit 13. Both sub units may be in the form of physically separate components, or program modules in a computer assembly. At the transmission end, the control and evaluation unit 7 has a control unit 14 which is likewise connected to the transmission/reception duplexer 8. The control and evaluation unit 7 may optionally contain feedback paths between the evaluation unit 11 and the amplifier 9 or the control unit 14. These optional feedback paths are indicated in FIG. 1 by dashed lines.

Figure 2:
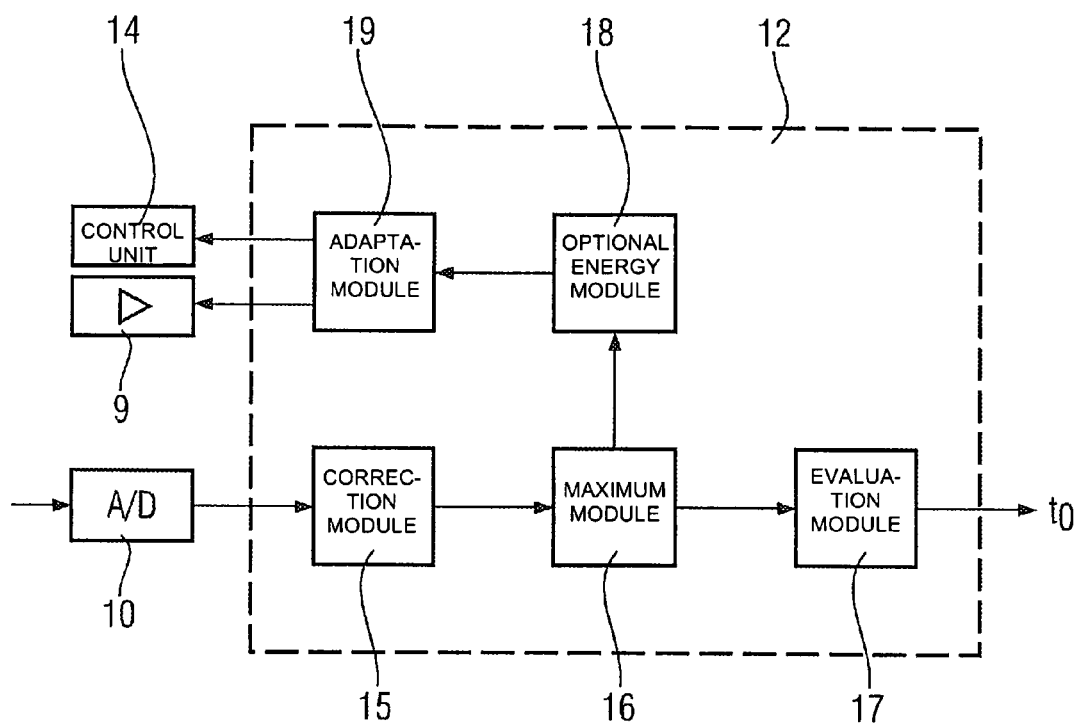
FIG. 2 is a block diagram of an exemplary embodiment of the sub unit for determination of the delay time in a medium as shown in FIG. 1, with adaptation of the transmission and reception condition.

FIG. 2 shows one exemplary embodiment of the delay-time sub unit 12. At its input, the delay-time sub unit 12 has a correction module 15, which is connected to the analog/digital converter 10. This is followed by a maximum module 16 and an evaluation module 17. An output path from the maximum module 16 is provided in the direction of an optional energy module 18, which is itself connected to an adaptation module 19. The last-mentioned modules 18 and 19 are components of the already mentioned feedback paths, which lead back to the amplifier 9, and to the control unit 14, respectively.

Figure 3:
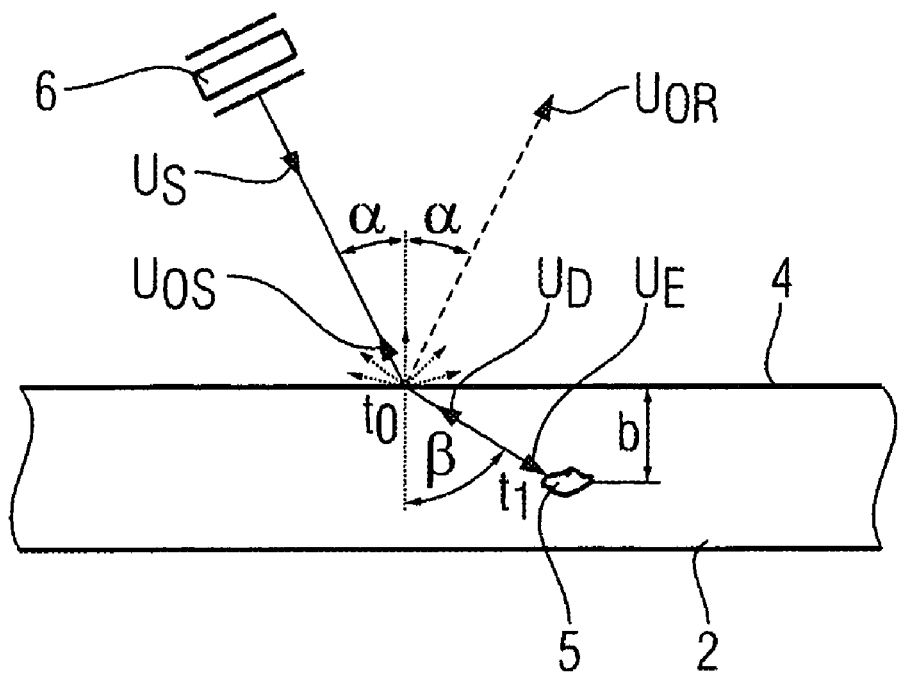
FIG. 3 is a schematic diagram of the ensonification of a surface of the component to be investigated with a checking sound beam.

The method of operation of the arrangement 1 will be described in more detail in the following text, with reference to FIGS. 3 and 4 as well.

Driven by an electrical transmitted signal $S_S$ produced by the control unit 14, the transmission/reception transducer 6 produces a checking sound beam $U_S$. The checking sound beam $U_S$ is directed obliquely onto the surface 4 of the component 2 to be investigated. This means that it forms an incidence angle a with the normal to the surface. Before arriving at the surface 4, the checking sound beam $U_S$ passes through the first medium 3.

On the surface 4, a part of the checking sound beam $U_S$ is reflected as a surface sound reflection $U_{OR}$ at a reflected angle of precisely the same magnitude as the incidence angle a. The surface sound reflection $U_{OR}$ does not pass back to the transmission/reception transducer 6.

A second component of the checking sound beam $U_S$ enters the component 2 as the injected sound beam $U_E$ at a refraction angle $\beta$, where it propagates in the direction of the defect 5. The refraction angle $\beta$ occurs because of the difference between the speeds of sound in the first medium 3 and in the component 2 to be investigated.

A third component of the checking sound beam $U_S$ is scattered on the surface roughness features which are normally always present to a certain extent. The scattered sound components are of a random character and are essentially oriented in all directions, so that they also form a response sound beam $U_{OS}$, which is scattered back. This passes back in the direction of the transmission/reception transducer 6, where it is converted back to an electrical received signal $S_E$.

In addition, the injected sound beam $U_E$ is passed back as the defect sound reflection $U_D$, after being reflected on the defect 5, in the direction of the transmission/reception transducer 6, this likewise resulting in a component of the electrical received signal $S_E$ which is converted back.

Figure 4:
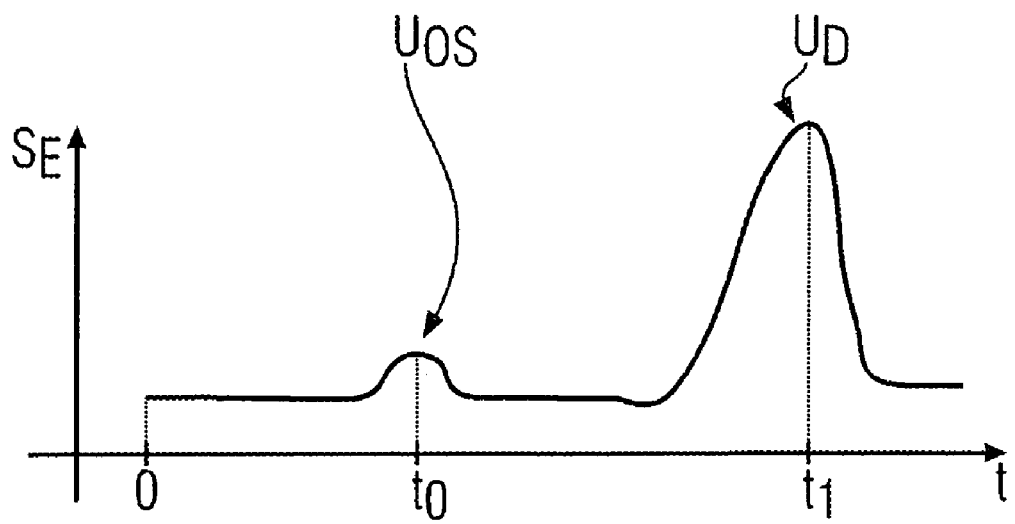
FIG. 4 is a graph of a time profile of a received signal with a scatter component from the surface of the component, and with a defect reflected component.

FIG. 4 shows a time profile of the electrical received signal $S_E$ plotted against the time t. The two components which result on the one hand from the scattering on the surface 4 ($U_{OS}$) and on the other hand from the reflection on the defect 5 ($U_D$) can clearly be seen in this time profile, as a first and a second maximum. The component which is dependent on scattering has a smaller amplitude, and may also be subject to major time fluctuations. The diagram shown in FIG. 4 is sometimes also referred to as the A image. Two-dimensional slices (=B images) and/or three-dimensional records of the component 2 to be investigated can be produced by successively scanning the entire surface. Either the component 2 (as indicated by the motion arrow in FIG. 1) or the transmission/reception transducer 6 is moved for this purpose.

The defect investigation of the component 2 is carried primarily by the sound propagation within the component 2. In contrast, the propagation path through the first medium 3 leads to corrupted results if it is not retrospectively compensated for in the control and evaluation unit 7, that is to say it is calculated out of the electrical received signal $S_E$. For this purpose, it is necessary to know or to determine the delay time in the medium which the checking sound beam $U_S$ and the backscattered response sound beam $U_{OS}$ require to pass through the first medium 3 in the forward direction and the return direction. This delay time in the medium is determined in the arrangement 1 on the basis of the backscattered response sound beam $U_{OS}$ in the delay-time sub unit 12. A time $t_0$ of the first response reflection (see FIG. 4) is in this case used as a measure for the sought delay time in the medium. Since this detected time $t_0$ records both the forward path and the return path, the delay time in the medium is essentially equal to $t_0/2$. The transmission and/or reception conditions are preferably varied until the component caused by the back-scattered response sound beam $U_{OS}$ in the electrical received signal $S_E$ is sufficiently large in order to be reliably detected as the first maximum that occurs.

Various measures are available for this purpose. The beam diameter of the checking sound beam $U_S$ can be reduced in order to achieve a certain amount of focusing on the surface 4. This can be done in particular by a transmission/reception transducer 6 in the form of an array test head. Furthermore, the amplitude of the electrical transmitted signal $S_S$ can be increased. In addition, the signal form of the electrical transmitted signal can be switched from a short pulse form to a burst signal form. The three measures mentioned are carried out within the control unit 14 and result in a more intensive backscattered response sound signal $U_{OS}$. A further measure relates to the reception conditions. A gain factor in the amplifier 9 can be raised so that the component of the electrical received signal $S_E$ caused by the backscattered response sound beam $U_{OS}$ is considerably increased.

These measures are taken automatically and on a requirement-controlled basis in the delay-time sub unit 12. The transmission conditions and reception conditions are adaptively matched by a control loop with a feedback path. The electrical received signal $S_E$ is subjected, for example, to requirement-controlled signal preprocessing, after amplification and analog/digital conversion in the correction module 15. Any error caused by oblique injection can optionally be compensated for. The received signals $S_E$ recorded for various positions of the component 2 are temporally stored for this purpose and collated to form a provisional B image. Space/time shifting is then carried out in order to compensate for the oblique ensonification.

Furthermore, rectification and smoothing can be provided in the correction module 15, for example simple magnitude formation and/or maximum formation with a sliding time window.

The signal which has been preprocessed in this way is then investigated for the first time maximum in the subsequent maximum module 16. In this case, relatively small maxima values or secondary maxima can be ignored, in order to improve the result. Furthermore, the results of the already investigated points on the surface 4 can also be taken into account in order to improve the confidence in the results. This is because, apart from surface areas close to the edge, adjacent points on the surface 4 lead to comparable delay times in the medium.

In principle, a two-dimensional method for deduction of the first maximum or of a maximum line can also be used in the maximum module 16. For example, the so-called watershed method may be used. It is also possible to investigate the determined maxima for spurious values. This is done, for example, by median filtering. After removal of the spurious result, smoothing is carried out, for example by averaging or FIR filtering. The smoothing process also allows a weighting factor to be taken into account, which may be in the form of the amplitude of the first maximum or of the area content under the first maximum in the electrical received signal $S_E$.

In the feedback path, the maximum module 16 is followed by the energy module 18, which is used to check whether the first maximum has already been identified with sufficient confidence. This is the case when the backscattered response sound beam $U_{OS}$ has an adequate energy content. If the energy module 18 finds that the detection confidence is still too low, the adaptation module 19 is instructed to appropriately adapt the transmission and reception conditions. By way of example, the transmission amplitude or else the time duration of the electrical transmitted signal $S_S$ is then increased. Furthermore, it is also possible to initiate one of the other measures that have already been described above.

Once transmission and reception conditions which result in a backscattered response sound beam $U_S$ with an adequate energy content have been found, the associated electrical received signal $S_E$ is subjected to final evaluation in the evaluation module 17, after passing through the maximum module 16, in order to determine the delay time in the medium, and thus the position of the surface 4 relative to the transmission/reception transducer 6.

An alternative embodiment (which is not illustrated), in which no feedback path is provided, also exists for the adaptive matching of the transmission and reception conditions as described in the exemplary embodiments in FIGS. 1 and 2. Instead of this, a fixed predetermined sequence of transmission and reception conditions is run through successively. The respectively detected electrical received signals $S_E$ are then evaluated for best-possible detection of the first maximum, and thus of the surface position. This refinement has particularly simple process control, and can easily be implemented retrospectively, even in already existing arrangements.

Once the delay time in the medium has been determined using one of the methods described above, the investigation of the component 2 for the existence of defects, as is actually of interest, is carried out in a second determination step. In this case, any component which may possibly be present in the electrical received signal $S_E$ and is caused by a defect sound reflection $U_D$ is investigated in more detail. A further maximum detection process is carried out for this purpose, and the defect 5 causing it is localized on the basis of the time $t_1$ of this further maximum (see FIG. 4), and taking into account the first time $t_0$ as determined previously. The evaluation is carried out using the relationship:

$$b = 0.5 \cdot c \cdot (t_1 - t_0) \cdot \cos(\beta) \qquad 5$$

with b denoting the defect depth of the defect 5 (=distance from the surface 4), and c denoting the known speed of sound in the component 2 to be investigated. The time $t_1$ thus symbolizes the total delay time that the checking sound beam $U_S$, the injected sound beam $U_E$ and the defect sound reflection $U_D$ require to travel in the forward and return directions.

The defect localization is carried out in the defect sub unit 13. The control and evaluation unit 7 is designed such that the process of determining the delay time in the medium and the defect localization can be carried out alternately, with the checking sound beam $U_S$ recording a different point on the surface 4 in each cycle, as a result of the movement of the component 2.

The arrangement 1 and the method for defect localization can be used for surfaces 4 of different shape, in which case both the delay time in the medium and the defect depth b that is actually of interest are identified reliably. The evaluation process can be carried out in real time. Furthermore, the implementation complexity is kept within limits. In particular, there is no need for any additional measurement device for separate recording of the distance between the transmission/reception transducer 6 and the surface 4.

What is claimed is:

1. A method for defect investigation of a component, comprising:
    acoustically irradiating a surface of the component obliquely, using a checking sound beam produced by a transmission/reception transducer, where the sound beam passes through a liquid or gaseous medium in which the component is immersed;
    receiving a response sound beam which is reflected back from the surface to the transmission/reception transducer;
    evaluating the response sound beam with respect to a signal runtime in the medium, taking into account the signal runtime in the medium between the transmission/reception transducer and the surface; and
    localizing a defect within the component by taking the signal runtime in the medium into account, the signal runtime in the medium and said localizing being alternately determined using at least one of an emission condition and/or at least one of a reception condition including:
        reducing a beam diameter of the checking sound beam to determine the signal runtime in the medium;
        increasing a transmission amplitude of the checking sound beam to determine the signal runtime in the medium;
        switching the checking sound beam from a short pulse form to a burst signal form to determine the signal runtime in the medium; and
        increasing a gain factor at a reception end to determine the signal runtime in the medium.

2. The method as claimed in claim 1, further comprising using a result of said evaluating for a change in at least one of the emission condition and/or at least one of the reception condition.

3. A system for defect investigation of a component immersed in a liquid or gaseous medium, comprising:
    a transmission/reception transducer producing a checking sound beam output to obliquely acoustically irradiate one surface of the component after passing through the liquid or gaseous medium, and receiving a response sound beam which is reflected back from the surface to said transmission/reception transducer;
    a control and evaluation unit, coupled to the transmission/reception transducer, evaluating a signal runtime of the response sound beam in the medium between the transmission/reception transducer and the surface;
    a determination unit, localizing a defect, taking the signal runtime in the medium into account, using at least one of an emission condition and/or at least one of a reception condition including:
        said transmission/reception transducer and said control and evaluation unit reduce a beam diameter of the checking sound beam for determination of the signal runtime in the medium;
        said transmission/reception transducer and said control and evaluation unit increase a transmission amplitude of the checking sound beam for determination of the signal runtime in the medium
        said transmission/reception transducer and said control and evaluation unit switch the checking sound beam from a short pulse signal to a burst signal for determination of the signal runtime in the medium; and
        said control and evaluation unit increases a reception-end gain factor for determination of the signal runtime in the medium.

4. The system as claimed in claim 3, wherein said control and evaluation unit further provides modifying of the emission condition and/or of the reception condition as a function of a result of evaluating the response sound beam.

5. The system as claimed in claim 3, wherein the evaluating of the signal runtime and the localizing of the defect are alternately performed.

* * * * *